(12) United States Patent
Benktzon et al.

(10) Patent No.: US 7,063,687 B2
(45) Date of Patent: *Jun. 20, 2006

(54) EYE FLUID APPLICATOR

(75) Inventors: Maria Benktzon, Sollentuna (SE); Henric Bjarke, Stockholm (SE); Carl-Göran Crafoord, Djursholm (SE); Hans Himbert, Bromma (SE); Stig Mannberg, Uppsala (SE); Ann-Marie Svensson, Bälinge (SE); Jonas Törnsten, Uppsala (SE)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 390 days.

This patent is subject to a terminal disclaimer.

(21) Appl. No.: 10/152,547

(22) Filed: May 21, 2002

(65) Prior Publication Data

US 2002/0193757 A1    Dec. 19, 2002

Related U.S. Application Data

(62) Division of application No. 09/088,726, filed on Jun. 2, 1998, now Pat. No. 6,423,040.

(60) Provisional application No. 60/052,246, filed on Jul. 11, 1997.

(30) Foreign Application Priority Data

Jun. 2, 1997   (SE)   ..................................... 9702082

(51) Int. Cl.
*A61M 35/00*   (2006.01)

(52) U.S. Cl. ..................... 604/294; 604/295; 604/301

(58) Field of Classification Search ................ 604/289, 604/294, 295, 296, 298, 300, 301, 302; 222/420–422, 222/215, 383.1, 523, 525, 527, 533, 556, 222/498
See application file for complete search history.

(56) References Cited

U.S. PATENT DOCUMENTS 1,846,763 A    2/1932   Schaefer (Continued)

FOREIGN PATENT DOCUMENTS

EP    0335513 B1    10/1989

(Continued)

OTHER PUBLICATIONS

Opticare® Advertisement.

*Primary Examiner*—Henry Bennett
*Assistant Examiner*—Camtu Nguyen
(74) *Attorney, Agent, or Firm*—Edward D. Robinson; Bryan C. Zielinski (57) ABSTRACT

An eye fluid applicator comprising a) a hand grip part having a distal end and a proximal end, the distal end and the proximal end defining a axis therebetween and a distal direction and a proximal direction along said axis, b) a container, or a seat for a container, having a bottle part and a delivery orifice for delivery of a stream or drops, the orifice defining a fluid delivery axis and a fluid delivery direction, along said axis, from the bottle through the orifice, the container being arranged with its orifice closer to the proximal end than the distal end, and c) an eye cup part having a rim and a cavity, the rim defining a contact plane, a contact axis normal to said contact plane and a contact direction, along said contact axis, from the cavity towards the rim, the eye cup being arranged at the orifice and the proximal direction of the hand grip and the contact direction of the eye cup forming an acute angle therebetween.

58 Claims, 2 Drawing Sheets

U.S. PATENT DOCUMENTS

| | | |
|---|---|---|
| 2,920,624 A | 1/1960 | Lerner et al. |
| 3,170,462 A | 2/1965 | Hall |
| 3,279,466 A | 10/1966 | Mings |
| 3,314,426 A | 4/1967 | Carroll |
| 3,872,866 A | 3/1975 | Lelicoff |
| 4,052,985 A | 10/1977 | Coleman et al. |
| 4,134,403 A | 1/1979 | Johnsen et al. |
| 4,792,334 A | 12/1988 | Py |
| 4,973,322 A | 11/1990 | Jewart |
| 5,201,726 A | 4/1993 | Kirkham |
| 5,366,448 A | 11/1994 | Basilice et al. |
| 5,578,019 A | 11/1996 | Feldman |
| 5,588,564 A | 12/1996 | Hutson et al. |
| 5,607,410 A | 3/1997 | Branch |
| 5,611,788 A | 3/1997 | Marchment |
| 6,423,040 B1 * | 7/2002 | Benktzon et al. ........... 604/300 |

FOREIGN PATENT DOCUMENTS

| | | |
|---|---|---|
| GB | 2255918 A | 11/1992 |
| TW | 252343 | 7/1995 |
| WO | 9606581 | 3/1996 |

* cited by examiner

EYE FLUID APPLICATOR

CROSS REFERENCE TO RELATED APPLICATIONS

This application is a divisional of application Ser. No. 09/088,726, filed Jun. 2 1998 now U.S. Pat. No. 6,423,040, which also claims the provisional Application 60/052,246, filed Jul. 11, 1997, the entire disclosure of which is hereby incorporated by reference.

TECHNICAL FIELD

The present invention relates to an eye fluid applicator comprising a) a hand grip part having a distal end and a proximal end, the distal end and the proximal end defining a axis therebetween and a distal direction and a proximal direction along said axis, b) a container, or a seat for a container, having a bottle part and a delivery orifice for delivery of a stream or drops, the orifice defining a fluid delivery axis and a fluid delivery direction, along said axis, from the bottle through the orifice, the container being arranged with its orifice closer to the proximal end than the distal end, and c) an eye cup part having a rim and a cavity, the rim defining a contact plane, a contact axis normal to said contact plane and a contact direction, along said contact axis, from the cavity towards the rim, the eye cup being arranged at the orifice.

BACKGROUND

Applicators for delivery of fluids, and in particular liquids, to the eye have been used since long for a great variety of purposes. The common eye bath for comfort, refreshment or rinsing may comprise a cup of anatomically adapted design for immersion of the eye. Delivery of large liquid amounts, usually by spray devices, has also been used in eye washes for example in emergency situations. The present invention is mainly concerned with applicators suitable for administration of relatively small amounts of fluids to the eye and also applicators of sufficient convenience in handling to facilitate or encourage frequent use, also in self-administration situations. A common application is the administration of medical to the eye. Typically the medical preparation has to be delivered in a fairly well defined volume to assure a specified dose to be delivered or absorbed. A large surplus cannot be allowed due to improper physiological effects from absorbency in non-target tissues or drainage of excess amounts through the tear channel into the throat cavity or the inconveniences caused by overflow on face and clothes. Also price considerations apply for expensive medications. As an example, the treatment of glaucoma requires frequent daily administrations of e.g. prostaglandins, beta-blockers or other expensive active ingredients, all having other then the desired pressure relieving action when absorbed by other body tissues than the eye. Moreover, proper administration of small amounts is complicated by the fact that the active ingredients cannot enter the eye but through the limited area of the cornea. Although the applicator to be described herein can be used with any fluid for any purpose, for convenience the invention will mainly be described in terms of medical applications.

The circumstances mentioned places severe demands on a applicator for the general purposes stated. The necessarily small preparation amount has to be positioned with great care in the eye not to invoke the dosing, overflow, side-effect and targeting errors mentioned. The positioning should be possible in at least one convenient patient posture for body, head and hand. Strained body positions are not only a convenience problem but may result in forced errors from stressed operation and trembling. It is desirable that the administration can be conducted in different body positions such as standing, sitting or lying, if possible also highly independent of applicator orientation. Equally important is a natural and relaxed arm and grip position during orientation, contacting and triggering. The device should also assist the user in delivering a precise volume of the preparation and not allow too small or large or inadvertently repeated ejections. Preferably a single design should fit varying anatomies without adjustments and should not induce fear for contact pain or discomfort. These requirements should be met both at patient self-treatment and operator assisted treatment. When the administration responsibility is placed on the patient simplicity is vital to suit also children, elderly and disabled persons, perhaps with reduced sight capabilities and hand strengths. On the contrary, an assistant might need to grip a device in a reverse hand position compared to the patient and may need supportive aiming means in replacement for patient tactile or visionary feedback. Finally a functional and convenient applicator device should meet several secondary demands, such as simple container refill or replacement, simple orifice opening and closure, ease of bottle identification and filling status control, open and cavity free construction for simple cleaning, overall design suitable to use and carry around in daily life and low costs for manufacture and assembly.

Prior art devices have only to a limited extent been able to fulfill the demands stated. Generally, devices for delivery of large fluid volumes are of little assistance in solving the delicate convenience, positioning and dosing problems in small volume delivery applications. As an example, the U.S. Pat. No. 1,846,763 discloses an eye bath for repeated use of an antiseptic rinsing liquid, the device having an inclination between a flask and an attached eye cup for the purpose of relieving the eye from flask weight in use but with no assisting features for any of the other purposes mentioned. In broad terms existing eye fluid applicators for small volumes are based either on drop or on spray delivery principles. Drop applicators rely on impact by gravity, typically after eye centering with an eye cup or eyelid retractor, after release e.g. by squeezing a resilient bottle. The drop method as such gives a concentrated delivery if properly positioned and is generally not experienced as uncomfortable but is not independent of applicator orientation. Common designs are not sophisticated and give little control over, and allow limited variations in, the administration sequence. Devices having parts to conform with face parts are described in U.S. Pat. Nos. 3,872,866, 4,134,403 and 4,792,334 although of unsuitable relative orientation and with no assisting hand grip part. A device example is disclosed in the patent specification EP 335,513, providing minimum support means with a hand grip type squeeze assistance but no other relief and improper orientation of the hand grip. A similar device is sold under the trademark "Opticare". Spray applicators rely on a shower, typically released by use of a manual lever, centered on the eye with similar means as for drop applicators. The spray method as such is highly independent of applicator orientation and may give a distributed impact but is limited to very small treatment amounts before losses occur in aerosol form and the application tend to release blink reflexes. Common designs do not cope with these problems or the general demands outlined. The U.S. Pat. No. 5,201,726 discloses a device example of this kind, having extensive means for draining off non-targeted and non-condensed surplus liquid, rather than preventing its occurrence. Although provided with hand grip and trigger the device is not ergonomic for use by patient or assistant.

Accordingly there remains a need for eye fluid applicators better meeting the specific and general design demands explained.

SUMMARY OF THE INVENTION

A main object of the present invention is to provide an eye fluid applicator meeting the general demands described hereinabove better than hitherto known devices. A more specific object of the invention is to provide an applicator suitable for convenient and precise delivery of small volumes to the eye. Another object is to and fluid surplus, overflow or losses. Still another object is to increase the tolerances for placement of the preparation in the target area of the eye. A further object is to allow treatment in varied body postures. Yet another object is to relieve the patient from strained body positions and requirements for skill and physiological capabilities. Another object is to provide a dispenser assisting the user in delivering dosed amounts. A further object is to provide a device suitable for use either by patient or assisting personnel. Still another object is to provide an applicator of suitable secondary properties, outside the immediate treatment situation, such as recharging, initiation, control, cleaning, handling and manufacture.

These objects are reached with the characteristic features set forth in the appended patent claims.

The applicator of the invention utilizes in the first place the basic principle of delivering one or several droplet directed towards the eye in order to allow small volumes to be delivered. Generally the applicator comprises a hand grip, a container and an eye cup, all with principal axes and directions as initially stated and further explained below. By forming an acute angle between the proximal direction of the hand grip and the contact direction of the eye cup an optimized relationship is achieved by the two contradictory requirements of on one hand avoiding the improper anatomical situation of lifting arm and hand maximally to line up a coaxial arrangement of the parts with the receiving direction for the eye and on the other hand providing sufficient space between hand grip and face to conveniently maneuver the device and its controls, such as a triggering button. In fact, if a persons hand in entirely relaxed condition is placed in front of the face the hand grip will naturally occupy exactly the acute angle described in relation to the sight line of the eye. Still the grip is not locked to one alternative only but several grips are available with about equal convenience to the user, such as with the fingertips or closed with full palm contact, both compatible with easy access to a triggering button placed on any side of the hand grip. The comparatively low arm position in relation to the body give plenty of room and margins for maintained relaxed grip when leaning the head backwards, for example to assist in drop delivery without need for lying down. It should be observed that although the grip relation described has similarities with that of a gun or tool, the present situation is entirely different since the hand position relative a protruding eye cup here is quite the opposite. Yet, this very circumstance satisfies the stated object of an applicator being equally suitable for use by an assistant operator, as the assistant will naturally use the standard grip for a gun or tool in directing the applicator towards the patient. Similar considerations apply for the angular relationship between the proximal direction of the hand grip and the orifice fluid delivery direction. If the orifice is part of a container separate from the hand grip, for example in the form of a miniature bottle, several of the secondary objects are within reach. The bottle can easily be attached and replaced at the proximal end of the hand grip, with its orifice free for opening and with at least a side and bottom end accessible for inspection. If the applicator is placed with its distal end on a support the bottle content will naturally drain away from the orifice, reducing contamination problems. An acute angle between the orifice fluid delivery direction and the eye cup contact direction serves to reduce the requirements for head leaning during drop delivery, improving comfort and broadening the application range. A resulting slightly tangential, rather than radial, drop impact on the eye may additionally serve to reduce the sensation and can advantageously be combined with a lower eyelid retractor to keep the liquid within eye boundaries. An eccentric arrangement between the orifice fluid delivery axis and the eye cup contact axis, with a more proximal position for the orifice, strongly increases the chances for proper delivery by broadening the acceptable target area to all the way between the eccentric and upwardly displaced eye position down to the lower eyelid. It is clear that the advantages described can be used in various combinations to achieve combined, synergetic or multiple advantages for diverse purposes.

Further and more specific objects and advantages will be evident from the detailed description hereinbelow.

DETAILED DESCRIPTION

General

As indicated in the introduction the applicator described herein may be used for a variety of purposes within and beyond the medical area and for any type of preparations, such as chemicals, compositions or mixtures in any container and delivered for any purpose. For reasons outlined the system has certain special values in connection with medical delivery devices where also the design constraints arm more severe than in most other applications and in which context the invention is mainly described.

The principles of the present invention may be used for eye applicators and systems in broad terms. The container content material shall be deliverable through an orifice, with or without use of a pump mechanism, and any material fulfilling this requirement can be used. Particulate or powder compositions, with or without a liquid or gaseous carrier media, can be delivered with use of known delivery mechanisms. Normally, however, the material is a fluid and preferably a liquid, including materials behaving as liquids such as emulsions or suspensions. These observations relates to the final preparation whereas other components, notably solids, may be present before final preparation. The nature of container content shall also be understood to include medical in broad terms and to embrace for example natural components and body fluids prefilled or drawn into the container although most commonly the medical is factory prepared. As indicated in the introduction the invention can with advantage be used for example with preparations for the treatment of glaucoma.

The preparation may be delivered towards the eye in the form of a coherent stream. It is preferred, however, that the preparation is delivered in the form of one, several or multiple discrete particles. Depending on the nature of the preparation, as described, the particle may be solid or preferably liquid for which purpose the concept "drop" etc. shall be understood to include also particles unless otherwise indicated. Common to the drops so defined is their shape is determined by inherent properties, solid particles by their permanent shape and liquid drops by their drop shape determined by surface tension criteria. This in contrast to a stream, the shape of which is determined by dynamically and non-stable factors. The principal force used to accelerate the drops towards the eye defines the general delivery principle utilized. The preferred principles are gravity delivery and kinetic delivery, with initial trajectory defining drop speed, notably spray delivery, the respective advantages of which have been discussed and can be utilized in different applications and for different purposes. Although spray delivery can be made virtually totally independent of applicator orientation, drop delivery by gravity benefits in a special way from the flexibility, with precision, introduced by the current invention.

The Eye Cup

Many of the advantages provided by the present invention are exploitable also without an eye cup part of the applicator, provided the operator take responsibility for device orientation and stabilization. It is preferred, however, that an eye cup part is included to relieve the operator from these responsibilities. A suitable eye cup part for the applicator comprises at least a rim and a cavity.

The purpose of the rim is to give a contact between applicator and face for and preferably also a self-centering of the applicator in the intended position relative the eye. The contact can be against any part of the face such as the forehead, nose and chin but a generally better centering is obtained if the rim make contact with the eye socket. The "rim" shall be understood in broad sense as the point or points of contact and need not be shaped as an edge or other elongated part but shall provide at least one point of contact preferably two, three or several points distributed in two dimensions for best centering. The points can with preference be shaped as one or several continuous edges and most preferably as a continuous loop. For purposes of description it is assumed that a line can be drawn so as to connect the contact points into a "contact curve", representing also theoretical face contact points not being actually contacted by the rim and in case of a closed continuous rim the contact curve and rim edge are assumed to coincide. A plane drawn to contain the contact curve forms a theoretical "contact plane". A line drawn normal to the plane forms a "contact axis" and a "contact direction" along the axis from the applicator towards the eye or, expressed in another way, from the cavity towards the rim. The contact axis and contact direction shall be regarded "symmetrical" if, in device related terms, they are centered within the contact curve or if, in patient related terms, they are radial to the eye ball. Suitable rim forms are known in the art and are not very critical to the invention. It is preferred to use a rim shape with left/right symmetry to make it equally usable for both eyes with a similar grip. A rim having a contact curve substantially in the form of an ellipse, adapted in size and shape to the eye socket, can for example be used. The contact plane through such a generally ellipse shaped form can be flat although frequently slightly curved along an axis parallel with the short axis of the ellipse. The rim can in a known manner with preference have eyelid retractor protrusions, preferably in the contact direction, for specific contact with at least the lower, but preferably also the upper, eyelid for the purpose of displacing and retaining the eyelids. Constructively the rim can have a soft edge for comfort and preferably a material of high friction, at least on any eyelid retractor part. The rim may be integral with the cavity part but is preferably a separate part attached, glued or fused to the cavity part for free material or color contrast selection.

The cavity serves the purpose of providing space within the contact curve boundaries for the protruding eye ball and also to secure a safety distance to the eye ball for any part in front of it, especially the orifice to be further explained. Accordingly the cavity shall be understood in broad terms for any construction meeting these objects. The cavity can be a true cup, as in known eye baths, but has no function as such and it is preferred that it has a more open design, e.g. to allow access to the orifice for opening and closing, to avoid preparation accumulation and facilitate cleaning, to allow an assistant operator to visually monitor orifice orientation and delivery, to facilitate manufacture. A minimum requirement is that the cavity construction provide supported attachment for the rim, e.g. a single arm or bar extending away from the rim in a direction opposite the contact direction, although two or several arms can be used for example in a cage-like design. With further details below, the eye cup shall be arranged at the orifice of the container in a manner allowing delivery of fluid to the eye and in particular within the contact curve of the rim. The relationship may depend on the delivery principle used, with special freedom at drop delivery, but generally it is preferred that the orifice is positioned behind, when seen opposite the contact direction, the contact curve and with a projection along the contact direction within said curve. The orifice can with preference point into or be arranged within the cavity, preferably with at least a fluid delivery direction component parallel with the contact direction. It is preferred that a certain safety distance is maintained between the orifice apex and the contact plane, to prevent contact with the eye ball for any foreseeable individual anatomy and to prevent patient fear for such contact, e.g. a distance of at least 5 mm, preferably at least 8 mm and most preferably at least 10 mm. The abovesaid support and attachment of the rim via the cavity construction can be made to the container or its orifice but it is preferred to attach the rim to the hand grip part, e.g. for allowing unobstructed replacement or the container.

The Container

The container for the preparation may contain a single dose for one time delivery to the eye, e.g. separate replaceable containers of single dose each or a band of such containers to be intermittently fed into the dispensing position of the device, perhaps connected to a counting device, as known per se e.g. from GB 2,255,918 or WO 96/06581. Commonly and preferably the container contains several doses for multiple administrations. The container generally comprises a bottle part and an opening for the preparation allowing the preparation to pass towards the eye.

The orifice may have different designs depending on which delivery principle is used. Generally, the last part of the orifice can be seen as a channel determining the flow direction for the fluid in said last part, hence defining a "fluid delivery axis" centered within said channel and its flow and a "fluid delivery direction" along said axis in the flow direction from the bottle through the orifice and towards the eye. In kinetic delivery, such as stream or spray delivery, the preparation will typically continue towards the eye in the fluid delivery direction also after release from the orifice. A seam will continue concentrated along the fluid delivery axis. Sprays can be given various shower shapes and diverging angles, depending on nozzle type and delivery pressure, and the shower will be seen as centered around the fluid delivery axis. The nozzle may need to have separate entrances for a carrier media, e.g. a pressurized gas, when needed and if not added earlier in the flow sequence. On the contrary, at drop delivery the drop or drops released at the orifice will continue in the gravity direction, allowing relatively free positioning of the fluid delivery direction in relation to the eye cup, but in the fluid delivery direction only when this is pointing vertically downwards, the latter being preferred for most simple design and safest positioning of the released drop. In drop delivery the orifice physical design can be very simple, e.g. an opening sufficiently narrow not to release more than a drop at a time, for control preferably only after some pumping action to be further described below.

The bottle part can be integral with other parts of the applicator such as the eye cup but preferably the hand grip part, e.g. so that the hand grip has a cavity for the preparation in a way known per se. It is preferred, however, that the bottle is a separate part which can be replaced in the device. Also the orifice part may be separate and replaceable, especially when the orifice construction is simple as in drop delivery devices, whereas more elaborate constructions may be reusable, e.g. kinetic nozzle types. There may be a conduit, such as a tube, between the bottle and the orifice, e.g. a tube extending to the bottle bottom to allow a very free positioning relative the orifice. Most simple design is obtained with a bottle having an opening connected directly to the orifice. The bottle shape is not critical but in broad terms the bottle has a symmetry axis from bottom towards its opening. Said axis may have any angle relative the fluid delivery axis as defined, for example a right angle or an obtuse angle. It is preferred, however, that the bottle symmetry axis is substantially parallel with, and preferably coaxial with, the fluid delivery axis, which assists in complete emptying of the bottle and reduced contamination flows around the bottle. The bottle design as such is not very critical. However, there are some advantages in using bottle designs having a non-cylindrical cross-section perpendicular to its said symmetry axis and preferably a non rotational symmetry cross-section having a broad axis and a narrow axis as represented by, but not limited to, a roughly rectangular cross-section. Such bottle structures have better emptying and contamination preventing advantages, as discussed, and additionally provide better bottle type identification and filling status advantages, to be further explained below.

In addition to the minimum requirements discussed the container component may incorporate other features for convenience. Commonly the orifice is closed between individual administrations, typically by screwing an opening cap to the orifice, in order to prevent leakage or contamination. Even this simple operation may cause problems to a disabled patent having limited hand strength. Accordingly it is known to include with any preparation bottle a cap opener, integral with or separate from, the cap and generally providing a leverage assisting the patient by reducing the force necessary for opening an closing the bottle. The present invention provides some assistance in these respects, e.g. by making the orifice accessible via the open design of the eye cap cavity already described or by providing means on e.g. the hand grip part for facilitating the bottle opening, to be further described.

The Hand Grip

The hand grip serves to provide a convenient grip for the user and to form an attachment for at least one of the other parts. The hand grip can have any shape such as spherical in two or three dimensions, loops for the fingers or the whole hand etc. It is preferred that the hand grip has a generally elongated form, which can be accommodated in the closed palm or held by the fingertips. Like for the eye cup it is also preferred to use a general left/right symmetry, when seen in the contact direction, for use with either hand and for both eyes. The elongated form shall be understood in broad sense from a symmetrical cylinder to a more or less complete adaptation the anatomy of the hand or arm or having aesthetic or practical features over those dictated by the grip as such. Independent of shape one part of the hand grip will necessarily be intended to be held closer to the eye and another part farther away from the eye and these parts will be referred to as "proximal end" and "distal end" respectively, with a corresponding "proximal direction" and a "distal direction" respectively. Said ends will define a "hand grip axis" therebetween. For positional statements the hand grip axis shall be regarded substantially centered within the hand grip. For very complex hand grip shapes centering of the axis may not be straightforward but in device related terms the centering shall then be regarded related to parts especially designed for gripping or otherwise generally to the parts closest to the eye cup, which are most easily used for gripping. In user related terms the centering shall be regarded related to the grip axis of the palm when using the device.

The eye cup will be positioned closer to the proximal end of the hand grip than to the distal end and preferably at the extreme proximal end thereof. It is also preferred that the eye cup is arranged with a lateral distance to the hand grip to give room between hand and face, i.e. the eye cup is displaced in the contact direction from the hand grip axis. Expressed as the normal distance from the hand grip axis to the contact curve point, or rim part, located most towards the distal end this distance can be at least 1 cm, preferably at least 2 cm and most preferably at least 3 cm. The distance is generally less than 15 cm, preferably less than 12 cm and most preferably less than 10 cm. For elongated hand grip designs these distances preferably relative the grip front towards the eye cup, rather than relative the grip axis,. Since the container orifice may point into the eye cup similar conditions apply for the orifice, e.g. it is preferred that also the orifice is located closer to the hand grip proximal end and with a lateral distance to the hand grip axis although the distance can be smaller with the safety distances earlier described. If the container is attached to the eye cup it need not be attached to the hand grip but it is generally preferred that the container is attached to the hand grip, directly or indirectly e.g. via the orifice part. A cavity within the hand grip may serve as the container or at least the bottle part of it. For reuse of the applicator part it is preferred that the container, or at least the bottle part of it, is a separate part and replaceable. In the latter case it is preferred that the hand grip comprises a seat for the container on, or preferably within, the hand grip. It is preferred that the bottle is positioned so that it is at least partially exposed, preferably so that the label thereof, and preferably its filling status, can be read and monitored respectively by the user, for which purposes openings or transparent windows can be arranged at critical positions on the hand grip. The most flexible positioning of the container is possible if there is a conduit, e.g. a suction tube, between the container bottle part and the orifice and the bottle can be placed essentially anywhere. It is preferred, however, especially when the bottle forms a directs continuation into the orifice, as for example in drop delivery or when bottle symmetry axis and orifice axis are coaxial, that the container seat is located at the proximal end of the hand grip. This position is suitable for the initially mentioned draining and accessibility aspects but also for the abovesaid bottle exposure purposes and more so if the flat design described, having broad and narrow axis, since insertion is facilitated and larger side and bottom surfaces can be exposed, especially if the bottle is arranged with its narrow cross-section axis more parallel with the hand grip axis than its broad axis.

When the container or bottle is attached to the hand grip it is preferred to use means allowing simple replacement. When the orifice part is more or less permanently arranged on the applicator and only the bottle part is replaced it may be sufficient to attach the bottle to the orifice by any known closure type, such as threads, bayonet, luer, friction, snap lock or any other fit. In case the bottle is replaced together with the orifice the bottle and/or orifice part may need to be accommodated in the seat. In both situations there are some advantages in enclosing at least a part of the container within the hand grip part, for example to save space, protect the bottle and its position, allow use of squeezable bottles etc. For this purpose the container may be introduced into the hand grip through an opening therein although it is generally preferred to divide the hand grip into at least two parts, which can be separated and again closed, e.g. via separation or preferably via a hinge mechanism. When the bottle seat is buried deep within the hand grip it may be desirable to divide it over an entire cross-section, e.g. substantially perpendicular to its axis but preferably with a plane along its axis. When the container seat is at the proximal end an advantageous design, facilitated by the angle conditions of the invention, is to make the proximal top part openable, e.g. by a section substantially perpendicular to the hand grip axis and most preferably with a section having substantially the same angular relationship to the hand grip axis as the fluid delivery axis or bottle axis as defined to the hand grip axis. The connection between the openable hand grip parts can be of any known type, such as entirely separate, a hinge mechanism or a rail mechanism for shearing movement of the parts in said section or a combination thereof. Preferably the opening arrangement comprises a convenient locking and release mechanism, e.g. incorporating a release key. The various sections and divisions, singly or in combination, may additionally serve to enable an opening of the hand grip for cleaning or inspection.

When the eye cup is attached to the hand grip the physical connection can be made at any point of the had grip but preferably to a proximal part thereof. When the hand grip is divided for insertion of the container it is preferred to attach the eye cup to the proximal part of the division. The eye cap can generally be an integral part of the hand grip or its parts but is preferably made as a separate component, permanently or releasably attached, e.g. for separation in connection with cleaning, transport, replacement or for adjustability, for example in eye to orifice distance to provide adaptations to different anatomies or safety requirements.

The hand grip may comprise further assisting details. It is preferred to design the distal end with a foot, enabling stable placement of the applicator on a flat horizontal support preferably so that the hand grip axis, and most preferably its symmetrical axis, has a substantially vertical component within the stability requirement. The foot may comprise a distal end flat part, perhaps with a broadening or increased weight to lower the point of gravity. The hand grip may have internal volume and external surfaces that are unused for its primary purpose and can be utilized for other purposes. A hole or other grip adapted to a bottle cap can be provided as a tool assisting in opening and closure, preferably arranged at the distal end and under the foot when present. The hand grip can also with preference comprise a pump mechanism to be further described below.

Pump Mechanism

The applicator as described can be used without any particular pump mechanism, e.g. by gravity delivery from an orifice of sufficient width to give a stream or individual drops. It is preferred, however, to include a pump mechanism in the applicator, e.g. to get better control over the release moment and dose amount or to enable alternative delivery methods.

The pump mechanism for delivery of preparation through the container orifice should basically include at least one type of pump which may have to be selected for the special kind or container and preparation type used. The pump may include any kind of pressure source, such as mechanical or electrolytic pressure build-up, in the container and suitable valve means for control, which method can be used with virtually any kind of container and any kind of product, including powders when carried by a media and delivery through liquid streams or drops. If the bottle at least partly and preferably substantially totally is resilient the common method of squeezing to establish overpressure can preferably be used, especially in low demanding applications such as low speed drop delivery. In more demanding applications, e.g. in view of dosing, delivery speed, atomization, preparation viscosity etc. such as in spray delivery, pumps based on controlled positive displacement are preferred, e.g. pumps based on peristaltic action, membrane type pumps but preferably pumps based on a separate cylinder and piston action, either with one way action as in a syringe or repeated action as in suction and ejection type pumps. Most pumps types mentioned are compatible with either a tube connection between the orifice and another container part or a direct connection between bottle and orifice, provided these parts are held in proper relationship for fluid flow towards the orifice. Several containers with the same or different pump mechanisms may be provided, for example to separately deliver the preparation and a carrier media or a driving and atomizing media. The energy required for the pump action can be stored in any known form, such as gas pressure, vacuum, hydraulics, springs etc. although manual operation is mostly sufficient and preferred.

The pump mechanism may also include a manual control, forming the interface between user and actual pump movement. In case of stored energy the control may take the form of a trigger, releasing e.g. a valve or a mechanical lock. In case of manual operation the control may take the form of an actuator, directly or via a link system performing the pump movement. Preferably a link system incorporates a lever arrangement which may be used to reduce the manual force applied, e.g. in case the preparation is too easily expelled or if a reduced stroke length is desired, but preferably is used to amplify the manual force or increase the stroke length for the actuator. The manual control may include common safety details such as an arming lock or command requirements making the device child proof.

It is preferred that the pump mechanism also incorporates means for controlling the dose delivered and for reducing the risks for undue over, under and repeated dosing. Dose control may be arranged with the pump proper, especially when stored energy is used. A valve may be controlled by opening time or sluice volume and movable pump parts by allowable displacement range. Dose control can alternatively and preferably be arranged with the manual control means, especially when these take the form of an actuator, by similarly limiting stroke length or pressure. A preferred link system of this kind incorporates an upsetting type of lever, initially having a curved configuration that is straightened by lateral forces applied to the bend, which mechanism provides a predefined limited possible elongation in addition to a leverage and optionally a tactically sensible relief after passage of the critical displacement.

The pump mechanism can be arranged on or at the container it is generally preferred to arrange it at or in the hand grip, e.g. to facilitate container replacement. The manual control can be positioned fairly freely on the hand grip and still be conveniently accessible for a user, e.g. on the far side relative to the eye cup position but it is generally preferred to arrange it on the close side relative to the eye cup.

Part Relationship

According to the invention the applicator main parts shall have at least one of several possible spatial relationships to give the advantages indicated. Angles described below are based on the 360 degree scale and given as the smallest angle between vectors in terms of the directions defined.

It is preferred that the proximal direction of the hand grip axis and the contact direction of the eye cup (grip/cup) forms an acute angle therebetween, i.e. an angle less than 90 degrees. Preferably the angle is less than 85 degrees, more preferably less than 80 degrees and most preferably less than 75 degrees. Preferably the angle is at least 20 degrees, preferably at least 30 degrees and most preferably at least 40 degrees. This acute angle requirement means that the distal direction of the hand grip axis will point between straight out from the eye contact direction and normal thereto down the face, both extremes unsuitable for reasons described.

Similarly it is preferred that the proximal direction of the hand grip axis and the orifice fluid delivery direction (grip/orifice) forms an acute angle therebetween. The preferred general limits for this angle are the same as given in the preceding paragraph for the grip/cup relationship. However, it is preferred that the grip/orifice angle is larger than the grip/cup angle, preferably at least 5 degrees and most preferably at least 10 degrees larger but preferably not more than 45 degrees larger and most preferably not more than 30 degrees larger. This requirement for a larger angle means that the orifice fluid delivery direction will be turned more towards the distal direction and the eye cup contact direction more towards the proximal direction, in relation to each other.

It follows that it is preferred that the orifice fluid delivery direction and the eye cup contact direction (orifice/cup) forms an acute angle therebetween, with preferred ranges as given for the "larger" angle in the preceding paragraph with the same preferred arrangement of having the eye cup contact direction on the proximal side and the orifice fluid delivery direction on the distal side relative the hand grip.

It is preferred that the orifice fluid delivery axis and the eye cup contact axis are mutually eccentric and that the orifice is positioned proximal in relation to the eye cup contact axis. Preferably the normal distance between the contact axis to the orifice tip is 2–20 mm, preferably 4–15 mm and most preferably 6–10 mm.

Use Method

The manner of using the applicator should be essentially clear from the description of its components with comments. A container integral with the device is first filled with the preparation or a separate bottle inserted into a seat on the device, possible after initial preparation steps such as a dissolution of a solid, and preferably with the bottle label exposed through any window provided. The replaceable bottle may have its own orifice or may require connection to an on-board orifice arrangement. A divided hand grip with may then need closing and locking. Before or after insertion a cap on the bottle or orifice may have to be removed, e.g. by any of the assisting means described. The user grips the hand grip and places the eye cup against the eye in a manner securing contact between the rim and a face part as the case may be. If the device operates with gravity delivery the user secures a substantially, but not necessarily perfect, vertical alignment of the orifice as defined, which may require a leaning of the head or body. If the device operates with kinetic delivery it may work in any head and body posture. If the device is equipped with a manual control, such as a knob, the user operates this control whenever desired after proper orientation of the applicator to deliver a dose of the preparation and the knob is released. These operations are similar both at self-administration and assistant supported operation although the grips around the hand grip may be slightly different. After use the applicator is preferably placed on its distal end foot or held with its hand grip axis vertical to drain liquid from the orifice. Generally the container contains multiple doses of the preparation and it is suitable to relocate a closure or protecting cap over the orifice to make the applicator fully transportable. At repeated use it may be desirable to confirm preparation type by inspecting bottle label and its filling status by inspecting its lower end through any window provided for this purpose. Any protection over the orifice is again removed and the process repeated. When the container is empty the bottle is removed by opening any division on the hand grip, possibly after releasing a key for a closure mechanism. Before inserting a fresh bottle it may be suitable to inspect the applicator for impurities or contamination's and perform a cleaning, for example by running the device in a dishwasher, followed by reassembly of parts for example by closing around hinges.

DESCRIPTION OF DRAWINGS

Figures 1, 2A, 2B, 3, 4, 5:
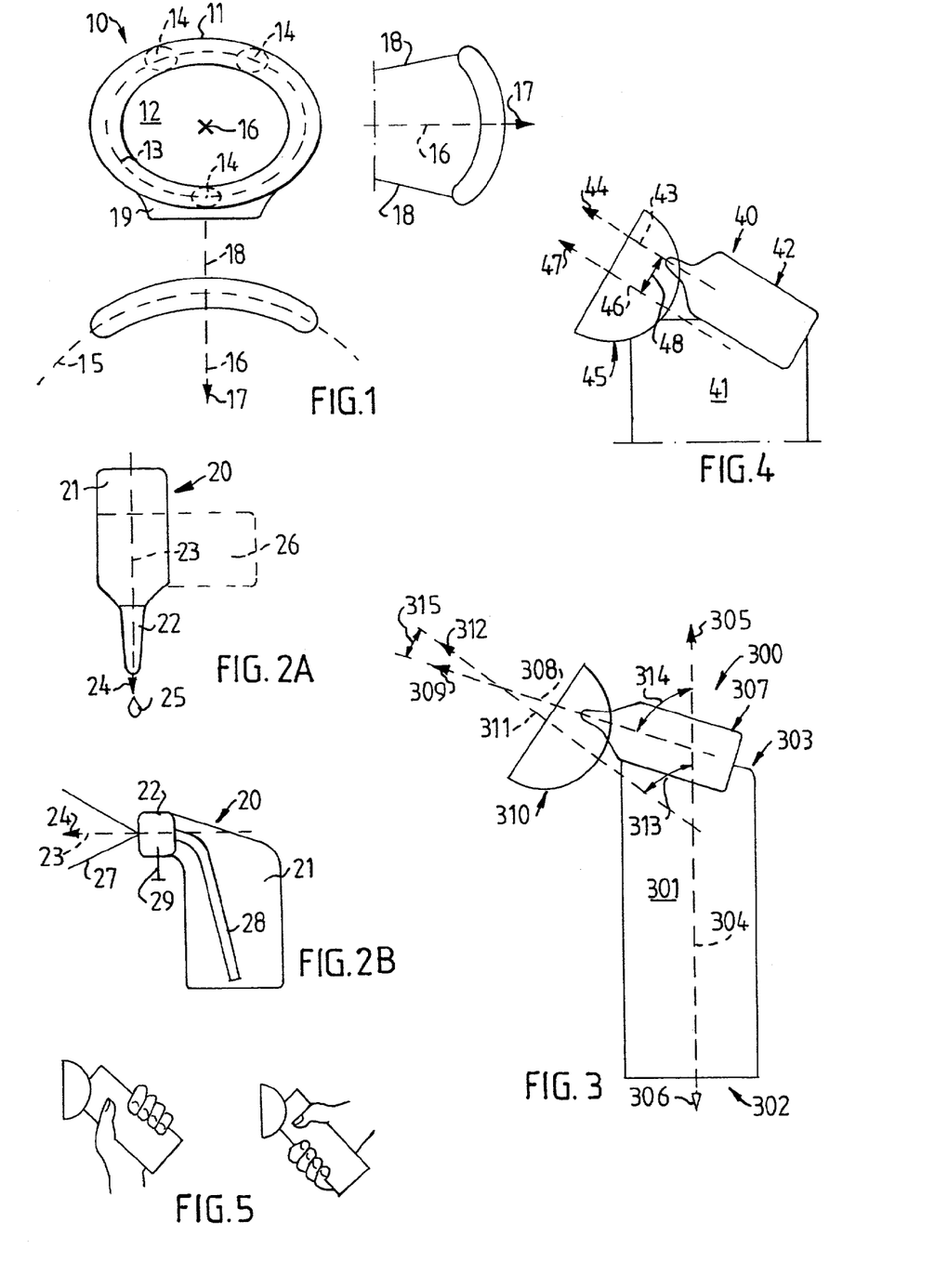
FIG. 1 shows in front, elevated and side view a schematic eye cup with rim and cavity.
FIGS. 2A and 2B illustrates schematically a container for gravity delivery and kinetic spray delivery respectively.
FIG. 3 illustrates schematically the applicator main parts and their principal spatial relationship.
FIG. 4 illustrates schematically an applicator with an alternative container to eye cup relationship.
FIG. 5 illustrates schematically possible hand positions at self-administration and assisted administration respectively.

In FIG. 1 an eye cup is generally designated 10, having a rim part 11 and a cavity 12. The rim has a generally elliptic form adapted for contact with the eye socket. Broken line 13 indicates a theoretical contact curve. Spots 14 indicate the option of using discrete contact points for the eye socket contour, rather than the closed and continuous rim shown, which would not alter the theoretical contact curve. The elevated view in the lower figure shows that the rim is slightly curved, roughly with maintained straight short axis but curved long axis of the ellipse, to bring the ellipse parts along the long axis closer to the eye. Broken line 15 indicates a theoretical contact plane, here normal to the Figure plane, in which plane the contact curve 13 lies and which contact plane also becomes curved. Normal to the contact plane and centered within the rim is shown in broken line a contact axis 16 with arrowhead 17 indicating a contact direction towards the hypothetical eye. The rim becomes curved also when seen in a side view as illustrated in the figure to the right. Schematic arms 18 extend from the rim 11 in a direction opposite the contact direction and serve as attachment for the rim. A schematic eye lid retractor 19 is also illustrated.

FIGS. 2A and 2B illustrates schematically a container for gravity delivery and kinetic spray delivery respectively. In both Figures the container is generally designated 20 and comprises a bottle part 21 and an orifice part 22, the orifice defining a fluid delivery axis 23 and a fluid delivery direction, indicated by arrowhead 24. The container of FIG. 2A is assumed to operate with gravity delivery as illustrated with drop 25. Although drop trajectory here coincides with fluid delivery direction in the orifice this may not be the case if the container is tilted form the vertical position shown. Phantom line 26 illustrates that the bottle part can have any angular relationship to the orifice although a bottle symmetry axis coaxial with the fluid delivery axis is preferred. The container of FIG. 2B is assumed to operate with kinetic delivery as illustrated by spray cone 27 in which cone the fluid delivery axis 23 and direction 24 are centered. An aspiration tube 28 is also illustrated, extending from orifice 22 to the bottle bottom. A schematic actuator 29 is assumed to be operated, directly or via a link system, to create the spray.

FIG. 3 illustrates schematically the applicator main parts and their principal spatial relationship. The applicator is generally designated 300. It comprises a hand grip part 301, generally having a distal end 302 and a proximal end 303, defining an axis 304 therebetween and a proximal direction, illustrated by filled arrowhead 305, and a distal direction, illustrated by unfilled arrowhead 306. Applicator 300 further comprises a container 307 the orifice of which defines a fluid delivery axis 308 and a fluid delivery direction, illustrated with arrowhead 309. Applicator 300 further comprises an eye cup 310, here shown with a flat contact plane and cup shaped cavity, the contact plane of which defines a contact axis 311 and a contact direction, illustrated with arrowhead 312. The main angles shown are the proximal direction of the hand grip axis 305 and the contact direction 312 of the eye cup (grip/cup) angle 313, the hand grip axis and the orifice fluid delivery direction (grip/orifice) angle 314 and the orifice fluid delivery direction and the eye cup contact direction (orifice/cup) angle 315. In the Figure all the angles stated, grip/cup angle 313, grip/orifice angle 314 and orifice/cup angle 315, are shown acute and, moreover, with the grip/orifice angle 314 larger than the grip/cup angle 313 and with the orifice fluid delivery direction 309 turned more towards the distal direction 306 and the eye cup contact direction 312 more towards the proximal direction 305, although other relationships are within the spirit of the invention.

FIG. 4 illustrates schematically an applicator with an alternative container to eye cup relationship. The applicator is generally designated 40 and comprises a hand grip part 41, a container 42, with an orifice fluid delivery axis 43 and fluid delivery direction 44, and an eye cup 45, with a contact axis 46 and a contact direction 47. The container 42 orifice apex has a distance 48 to the contact axis 46. It is further illustrated that the fluid delivery axis 43 and the contact axis 46 are roughly parallel and eccentric with the fluid delivery axis 43 more proximal than the contact axis 46.

FIG. 5 illustrates schematically possible hand positions at self-administration and assisted administration respectively. Although the arm positions are about 90 degrees different the grips are equally natural and relaxed.

Figure 6A:
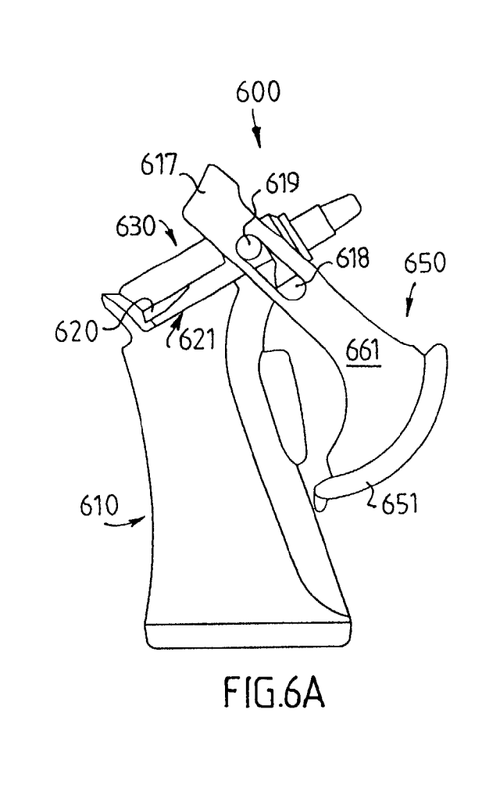
FIGS. 6A, 6B and 6C shows a preferred embodiment of the applicator, FIG. 6A showing the applicator in side view with a container seat exposed, FIG. 6B the applicator in side view when in position for use and FIG. 6C a section through the device as shown in FIG. 6B.
Figure 6B:
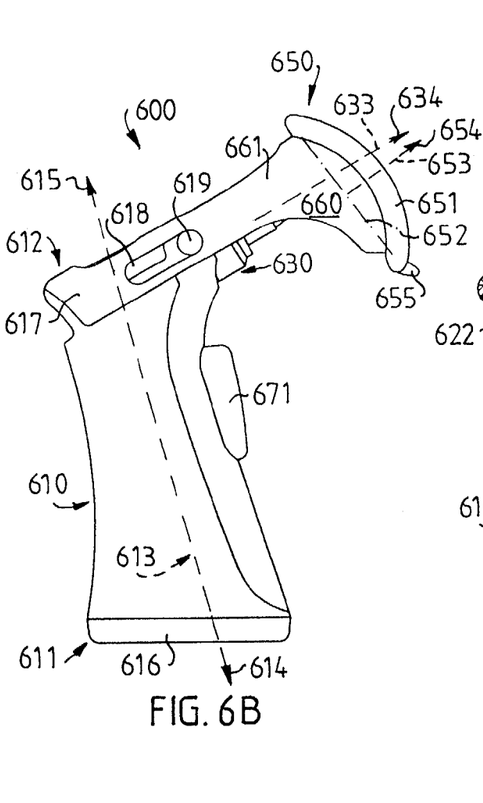
Figure 6C:
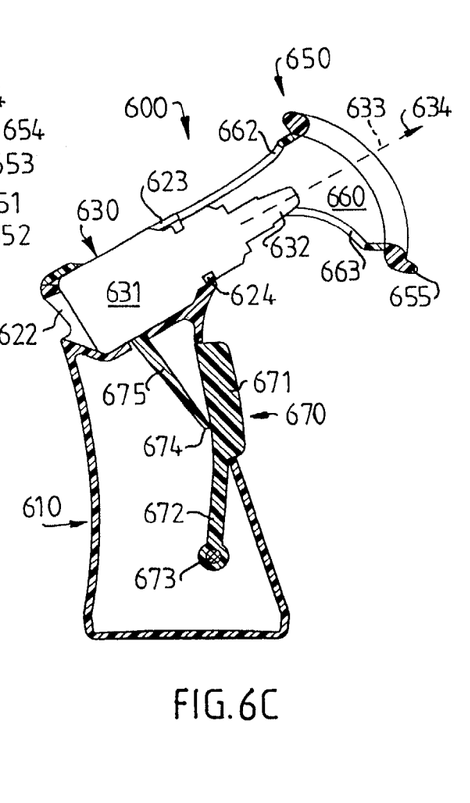

FIGS. 6A, 6B and 6C show a preferred embodiment of the applicator, FIG. 6A showing the applicator in side view with a container seat exposed, FIG. 6B the applicator in side view when in position for use and FIG. 6C a section through the device as shown in FIG. 6B. The Figures (A4 format) show the applicator in about its natural size. The applicator 600 main parts are a hand grip 610, a container part 630, an eye cup part 650 and a pump mechanism part 670. The hand grip can be said to define a distal end 611, a proximal end 612, a hand grip axis 613 with a distal direction 614 and a proximal direction 615. The hand grip distal end 611 is designed as a foot 616 for placement of the applicator with the hand grip axis in a roughly upright position. In a preferred embodiment the underside of foot 616 equipped with a hole adapted to an bottle cap to assist removal and attachment thereof. At the proximal end the hand grip is divided into an openable part 617 having slits 618, substantially parallel with the bottle axis, which slits cooperates with a stationary pins 619. From the open position shown in FIG. 6A the openable part 617 is turned around pins 619 and then pushed axially under engagement with stationary rails 620 and corresponding structures on the inner surfaces of openable part 617 to the position shown in FIGS. 6B and 6C with the pins 619 at the other end of slit 618. Opening of the openable part 617 exposes a seat 621 for the container 630 allowing insertion or removal thereof. The seat has a rear opening 622 exposing the bottle bottom, allowing inspection of bottle content, and openable part 617 has an upper opening 623, allowing inspection of bottle side, especially a label thereon. Attached to the openable part 617 is the eye cup 650 to be further described. The seat 621 accommodates and, after closure of the openable part 617, locks the container 630 by enclosing it in a cavity and by engaging a flange 624 under a container opening part. The container 630 generally comprises a bottle 631 and an orifice part 632, the latter defining a fluid delivery axis 633 and a fluid delivery direction 634. A bottle symmetry axis (not shown) is assumed to be substantially coaxial with the fluid delivery axis. The eye cup 650 generally comprises a rim 651 and a cavity 660. The rim 651 is roughly elliptical and slightly curved along an axis parallel to the short axis 652 and defines a contact axis 653 and a contact direction 654. A protrusion 655 serves as a lower eye lid retractor. The cavity 660 provides space for the eye ball and safety distance to the orifice 632. Lateral arms 661 connects the rim 651 to the openable part 617 by being an integral part thereof. An upper cavity opening 662 and a lower cavity opening 663 makes the cavity and orifice area accessible. In the applicator shown the grip/cup, grip/orifice and orifice/cup angles, as defined, are acute and the orifice tip slightly displaced in the proximal direction in relation to the contact axis. The applicator also includes a pump mechanism 670 including a manual control 671, being part of an arm 672 extending in the distal direction to a stationary axis shaft 673, around which the arm is pivotable, and in the proximal direction from a living hinge 674 on the inner side of the manual control 671 via a push rod 675 to the lower side of bottle 631. Operating the manual control 671 makes the push rod 675 exert pressure on resilient bottle 631 to expel fluid followed by return of the pump mechanism parts to their initial positions in an upsetting type movement. It is clear that the push rod maximum displacement is limited to a full straightening of the arm 672 and push rod 675 and that the movements give a leverage amplification of the manual force applied. The applicator described can with preference be manufactured from moldable plastics. Suitably the integral openable part 617 and eye cup part 650 are molded in one piece, possibly with addition of a separate material for the rim 651. The hand grip part can be manufactured e.g. as two halves, separate or hinged, with a division as in FIG. 3C and possibly with the pump mechanism 670 as a further part.

The invention claimed is:

1. An eye fluid applicator, comprising:
 a hand grip part having a distal end and a proximal end, the distal end and the proximal end defining an axis therebetween, a distal direction, and a proximal direction along the axis;
 a container comprising a bottle part and a delivery orifice for delivery of a stream or drops, the orifice defining a fluid delivery axis and a fluid delivery direction from the bottle through the orifice along the fluid delivery axis, the container orifice being arranged closer to the proximal end of the hand grip than the distal end; and
 an eye cup part having a rim and a cavity, the rim defining a contact plane, a contact axis normal to the contact plane, and a contact direction along the contact axis from the cavity towards the rim, the eye cup being arranged at the orifice;
 wherein the proximal direction of the hand grip and contact direction form an acute angle therebetween.

2. The applicator of claim 1, wherein the grip/cup angle is less than 85 degrees.

3. The applicator of claim 1, wherein the grip/cup angle is at least 20 degrees.

4. The applicator of claim 1, wherein the eye cup rim is adapted to fit into an eye socket.

5. The applicator of claim 1, wherein the eye cup rim is substantially in the form of a continuous or discontinuous ellipse.

6. The applicator of claim 1, wherein the eye cup rim comprises at least one eye lid retractor.

7. The applicator of claim 1, wherein the eye cup is attached to the hand grip.

8. The applicator of claim 1, wherein at least the bottle part of the container is a part separate from the hand grip and eye cup.

9. The applicator of claim 1, wherein the bottle has a cross-section having a broad axis and a narrow axis in the cross-section plane and that the bottle is arranged with its narrow cross-section axis more parallel with the hand grip axis than its broad axis.

10. The applicator of claim 1, wherein the orifice is designed to give drop delivery.

11. The applicator of claim 1, wherein the hand grip comprises a seat for the container.

12. The applicator of claim 11, wherein the seat is arranged at the proximal end of the hand grip.

13. The applicator of claim 11, wherein the seat has openings at least partially exposing the bottle.

14. The applicator of claim 11, wherein the hand grip has an openable part exposing the seat.

15. The applicator of claim 14, wherein the openable part of the hand grip is at the proximal end.

16. The applicator of claim 1, wherein the hand grip has a foot at the distal end allowing the applicator to stand with the hand grip axis about vertical.

17. The applicator of claim 1, wherein the hand grip comprises a hole or other grip adapted to receive a bottle cap.

18. The applicator of claim 1, wherein the applicator includes a pump mechanism.

19. The applicator of claim 18, wherein the pump mechanism act by squeezing a container part.

20. The applicator of claim 18, wherein the pump mechanism is manually actuated.

21. The applicator of claim 18, wherein the pump mechanism comprises a manual control forming the interface between user and pump mechanism.

22. The applicator of claim 21, wherein the manual control is arranged on the hand grip at its eye cup side.

23. The applicator of claim 18, wherein the pump mechanism comprises a link system incorporating an upsetting type lever device.

24. The applicator of claim 18, wherein the pump mechanism comprises a dose limiter.

25. The applicator of claim 18, wherein the pump mechanism and/or orifice are designed to give drop delivery.

26. The applicator of claim 18, wherein the pump mechanism and/or orifice are designed to give kinetic delivery and preferably spray delivery.

27. The applicator of claim 1, wherein the proximal direction of the hand grip and the orifice fluid delivery direction, grip/orifice, forms an acute angle therebetween.

28. The applicator of claim 27, wherein the grip/orifice angle is less than 85 degrees.

29. The applicator of claim 27, wherein the grip/orifice angle is at least 20 degrees.

30. The applicator of claim 27, wherein the grip/orifice angle is larger than the grip/cup angle by at least 5 degrees but not more than 45 degrees.

31. The applicator of claim 1, wherein the orifice fluid delivery direction and the eye cup contact direction, orifice/cup, forms an acute angle therebetween.

32. The applicator of claim 31, wherein the orifice/cup angle is at least 5 degrees but not more than 45 degrees.

33. The applicator of claim 31, wherein the orifice fluid delivery direction is turned more towards the distal direction and the eye cup contact direction more towards the proximal direction.

34. The applicator of claim 1, wherein the orifice fluid delivery axis and the eye cup contact axis are mutually eccentric and that the orifice is positioned proximal in relation to the eye cup contact axis.

35. The applicator of claim 34, wherein the normal distance between the contact axis and the orifice tip is at least 2 mm.

36. The applicator of claim 34, wherein the normal distance between the contact axis and the orifice tip is not more than 20 mm.

37. The applicator of claim 1, wherein the normal distance from the hand grip axis to the contact curve point, or rim part, located most towards the distal end is at least 1 cm.

38. An eye fluid applicator, comprising:
a hand grip part having a distal end and a proximal end, the distal end and the proximal end, defining an axis therebetween, a distal direction, and a proximal direction along the axis;
a container comprising a bottle part and a delivery orifice for delivery of a stream or drops, the orifice defining a fluid delivery axis and a fluid delivery direction from the bottle through the orifice, along the fluid delivery axis, the container orifice being arranged closer to the proximal end of the hand grip than the distal end; and
an eye cup part having a rim and a cavity, the rim defining a contact plane, a contact axis normal to the contact plane and a contact direction along the contact axis from the cavity towards the rim, the eye cup being arranged at the orifice;
wherein the proximal direction of the hand grip and the orifice fluid delivery direction form an acute angle therebetween.

39. The applicator of claim 38, wherein the grip/orifice angle is less than 85 degrees.

40. The applicator of claim 38, wherein the grip/orifice angle is at least 20 degrees.

41. The applicator of claim 38, wherein the grip/orifice angle is larger than the angle between the proximal direction of the hand grip and the contact direction of the eye cup, grip/cup, by at least 5 degrees but not more than 45 degrees.

42. The applicator of claim 43, wherein the grip/orifice angle is less than 85 degrees.

43. An eye fluid applicator, comprising:
a hand grip part having a distal end and a proximal end, the distal end and the proximal end, defining an axis therebetween, a distal direction, and a proximal direction along the axis;
a container comprising a bottle part and a delivery orifice for delivery of a stream or drops, the orifice defining a fluid delivery axis and a fluid delivery direction from the bottle through the orifice, along the fluid delivery axis, the container orifice being arranged closer to the proximal end of the hand grip than the distal end; and
an eye cup part having a rim and a cavity, the rim defining a contact plane, a contact axis normal to the contact plane and a contact direction along the contact axis from the cavity towards the rim, the eye cup being arranged at the orifice;
wherein the orifice fluid delivery direction and the eye cup contact direction form an acute angle therebetween, and the orifice fluid delivery direction is turned more towards the proximal direction than the distal direction.

44. The applicator of claim 43, wherein the orifice/cup angle is at least 5 degrees but not more than 45 degrees.

45. The applicator of claim 43, wherein the grip/orifice angle is at least 20 degrees.

46. The applicator of claim 38, wherein the grip/orifice angle is larger than the angle between the proximal direction of the hand grip and the contact direction of the eye cup, grip/cup, by at least 10 degrees but not more than 30 degrees.

47. The applicator of claim 38, wherein the grip/orifice angle is less than 75 degrees.

48. The applicator of claim 38, wherein the grip/orifice angle is at least 40 degrees.

49. The applicator of claim 43, wherein the orifice/cup angle is at least 10 degrees but preferably not more than 30 degrees.

50. The applicator of claim 1, wherein the grip/cup angle is less than 75 degrees.

51. The applicator of claim 1, wherein the grip/cup angle is at least 40 degrees.

52. The applicator of claim 1, wherein the grip/orifice angle is less than 75 degrees.

53. The applicator of claim 1, wherein the grip/orifice angle is at least 40 degrees.

54. The applicator of claim 1, wherein the grip/orifice angle is larger than the grip/cup angle by at least 10 degrees but not more that 30 degrees.

55. The applicator of claim 1, wherein the orifice/cup angle is at least 10 degrees but not more than 30 degrees.

56. The applicator of claim 1 wherein the normal distance between the contact axis and the orifice tip is at least 4 mm.

57. The applicator of claim 1, wherein the normal distance between the contact axis and the orifice tip is not more than 10 mm.

58. The applicator of claim 1, wherein the normal distance from the hand grip axis to the contact curve point, or rim part, located most towards the distal end is at least 3 cm.

* * * * *